(12) United States Patent
Uchida et al.

(10) Patent No.: US 6,882,872 B2
(45) Date of Patent: Apr. 19, 2005

(54) BIOLOGICAL INFORMATION DETECTING PROBE, BIOLOGICAL INFORMATION MEASURING APPARATUS, FABRICATION METHOD FOR BIOLOGICAL INFORMATION DETECTING PROBE, AND METHOD OF MEASURING BIOLOGICAL INFORMATION

(75) Inventors: Shinji Uchida, Neyagawa (JP); Kiyoko Ooshima, Shijonawate (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 19 days.

(21) Appl. No.: 10/203,219
(22) PCT Filed: Feb. 6, 2001
(86) PCT No.: PCT/JP01/00822
 § 371 (c)(1),
 (2), (4) Date: Nov. 4, 2002
(87) PCT Pub. No.: WO01/58355
 PCT Pub. Date: Aug. 16, 2001

(65) Prior Publication Data
 US 2003/0109030 A1 Jun. 12, 2003

(30) Foreign Application Priority Data
 Feb. 7, 2000 (JP) .................................... 2000-029519
 Aug. 4, 2000 (JP) .................................... 2000-237018

(51) Int. Cl.$^7$ ................................................ A61B 5/00
(52) U.S. Cl. ........................................ 600/310; 600/316
(58) Field of Search ........................... 600/310, 322, 600/323, 314, 316

(56) References Cited
 U.S. PATENT DOCUMENTS
 6,128,091 A 10/2000 Uchida et al.
 6,241,663 B1 * 6/2001 Wu et al. .................... 600/310

FOREIGN PATENT DOCUMENTS
 JP 5-508336 11/1993
 JP 9-113439 5/1997
 JP 11-064216 3/1999
 JP 11-178799 7/1999
 JP 2601665 10/1999
 WO WO 92/00513 1/1992

OTHER PUBLICATIONS
 "Diabetes and BME" BME vol. 5, No. 8, 1991 pp. 16–21 (Japanese with English translation).

* cited by examiner

Primary Examiner—Eric F. Winakur
 (74) Attorney, Agent, or Firm—RatnerPrestia

(57) ABSTRACT

Provided are a biological information detecting probe and a biological information measuring apparatus that are easy to handle and can easily carry out highly accurate measurements by improving contact between a surface of a living body and a light sensor while minimizing damage to the body tissue, and a biological information measurement method for implementing the same. The invention also achieves a biological information measuring apparatus that can easily measure biological information concerning deep portions of a living body by improving contact between the surface of the living body and the light sensor, and a method for implementing the same. The biological information detecting probe comprises a raised portion 5 forming a recessed portion which is pressed against a living tissue in intimate contact relationship, a substrate 4, an exit end face 9 from which detection light exits through one part of the recessed portion, and a light receiving means 11 which is provided in another part of the recessed portion and into which the detection light is introduced, wherein with the raised portion 5 and substrate 4 held pressed against the living tissue, the detection light is passed through the living tissue and introduced into the receiving means 11.

46 Claims, 9 Drawing Sheets

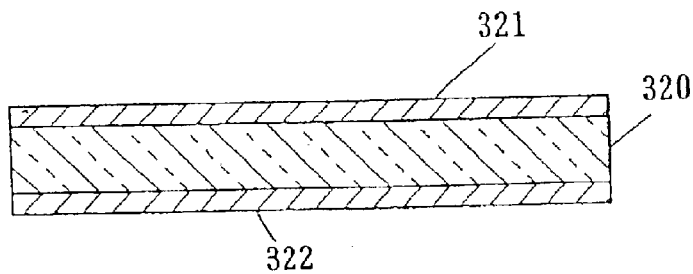
Fig. 4 (a)
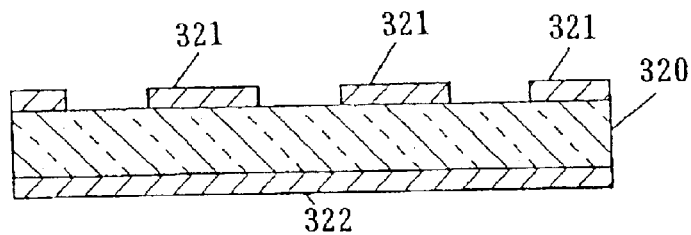
Fig. 4 (b)
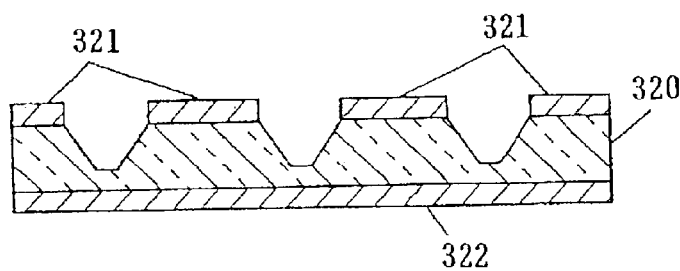
Fig. 4 (c)
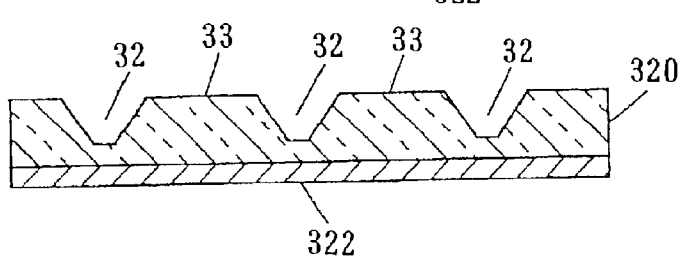
Fig. 4 (d)
Fig. 5
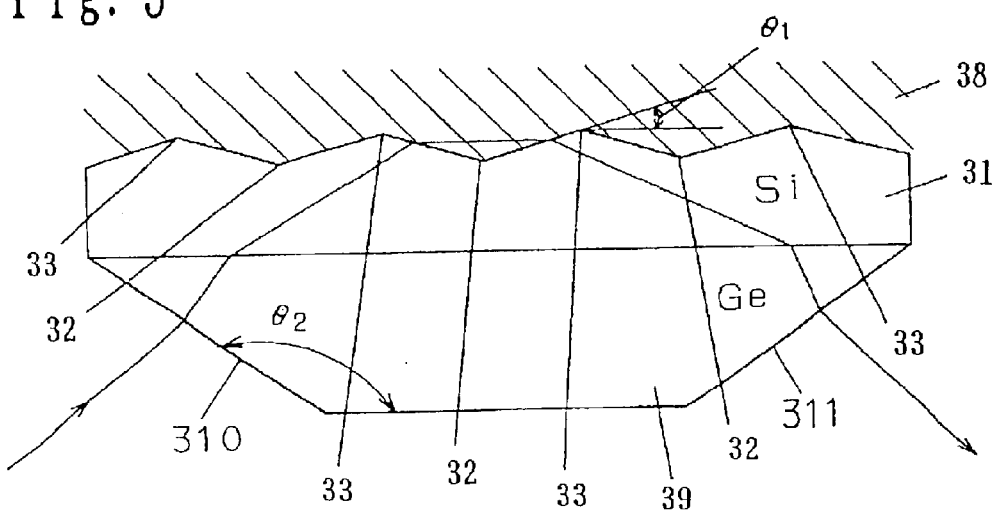

BIOLOGICAL INFORMATION DETECTING PROBE, BIOLOGICAL INFORMATION MEASURING APPARATUS, FABRICATION METHOD FOR BIOLOGICAL INFORMATION DETECTING PROBE, AND METHOD OF MEASURING BIOLOGICAL INFORMATION

This Application is a U.S. National Phase Application of PCT International Application PCT/JP01/00822.

TECHNICAL FIELD

The present invention relates to a biological information detecting probe and a biological information measuring apparatus form on invasively measuring biological information, such as glucose, blood sugar, water content, cholesterol, etc. in a living body, by measuring light diffusely reflected from the living body or light passed through a superficial tissue; the invention also relates to a fabrication method for such a biological information detecting probe, and a method of measuring biological information.

BACKGROUND ART

In the prior art, various types of apparatus have been proposed for noninvasively measuring the concentration of blood sugar in a subject.

In Japan Laid-Open Patent Publication No. 5-508336, for example, there is proposed a method for measuring the concentration of blood sugar in a human subject by using clear infrared radiation. According to this method, the subject is irradiated with near infrared radiation at wavelengths of 600 nm to 1100 nm, and the blood sugar concentration is obtained by analyzing specific wavelength components of the light passed through the subject.

While near infrared light has the advantage that it is suitable for analysis because, compared with infrared light, near infrared light is less strongly absorbed by water and therefore easily passes through aqueous solutions and living bodies, the disadvantages are that it is difficult to extract information concerning individual components because the absorption peaks of various components overlap in a complicated manner compared with infrared light, and that the absorption peak wavelength can easily change widely with temperature; with these and other disadvantages, the near infrared method has not yet been implemented commercially.

As opposed to that, Japan Laid-Open Patent Publication No. 11-178799 proposes a method for measuring glucose, water content, etc. in a superficial tissue of a living body by using near infrared radiation. According to this first prior art method, the superficial tissue of a living body, with a portion thereof raised, is placed in a single groove formed in a flat member; in this condition, near infrared radiation is emitted from an optical fiber bundle placed on one side of the raised portion, and is received by an optical fiber bundle placed on the opposite side of the raised portion. Then, a portion of the light diffusely reflected at the superficial tissue is detected and its spectrum analyzed, to obtain biological information, in particular, glucose, water content, etc. of the dermis tissue.

As a prior art example using mid-infrared radiation, there is proposed, for example, in Japan Laid-Open Patent Publication No. 9-11343, a method that uses an attenuated total reflection (hereinafter abbreviated ATR) measuring apparatus to measure specific constituents of a subject, especially, a living body.

A schematic diagram illustrating this method is shown in FIG. 11. As shown, a transparent ATR prism 20 having a pair of reflecting surfaces being parallel to each other on opposite sides thereof is placed in intimate contact with a lip mucosa 21 to measure the concentration of blood sugar. According to this method, the ATR prism is held in a mouth between the upper and lower lips, and the light emerging from the ATR prism 20 after undergoing attenuated total reflection at the interfaces between the lip mucosa 21 and the respective reflecting surfaces of the prism 20 is analyzed.

In BEME, vol. 5, No. 8 (Japanese Society of Medical Electronics and Biological Engineering, 1991), there is proposed a method in which, after an ATR prism formed from a ZnSe optical crystal or the like is placed in intimate contact with a lip mucosa, laser light at wavelengths of 9 to 11 microns is introduced into the prism and caused to undergo multiple reflections within the prism, and the absorbed light is analyzed to measure sugar blood and blood ethanol concentrations. According to this method, blood sugar and blood ethanol concentrations can be measured noninvasively in real time.

These methods use an evanescent wave (so-called seeping light) for quantitative analysis. As shown in FIG. 11, the light traveling through the prism 20 is reflected after its lightly penetrates into the lip mucosa 21. As a result, the light penetrating into the lip is affected by various constituents in the body fluid existing there. Therefore, by measuring the amount of reflected light, changes in the reflectance, absorptance, etc. of the body fluid can be detected, and each component in the body fluid can thus be obtained.

There is also proposed Fourier transform Raman spectroscopy that uses a laser light source such as an argon laser with an oscillation wavelength of 500 nm, a YAG laser with an oscillation wavelength of 1060 nm, or a semiconductor laser with an oscillation wavelength of 880 nm, irradiates a living tissue with the laser light emitted from the light source, and obtains biological information by detecting the light scattered within the living tissue (Raman scattered light) and by analyzing the spectrum of the detected Raman scattered light. According to this method, since the Raman scattered light has wavelengths characteristic of each individual kind of substance in the living tissue, the kinds of substances in the living tissue and their concentrations can be calculated by analyzing the spectrum of the Raman scattered light.

However, the prior art noninvasive blood sugar measuring apparatus described above have had the following problems.

The first prior art method has had the problem that if the optical fiber at the incident side and the optical fiber at the receiving side are not placed correctly opposite each other, the loss of light within the living tissue increases and the intensity of diffusely reflected light to be received decreases; furthermore, since the light penetrates deeply into the living tissue, there has been the problem that various diffusely reflected lights differing in optical path length, containing information not only on epidermis and dermis but also on deeper portions of the living tissue such as subcutaneous tissue, are detected.

Accordingly, when the target to be measured is skin tissue, it has been difficult to extract and measure biological information only on the superficial tissue of a living body, such as the epidermis about 100 to 200 microns thick and the underlying dermis about 500 to 1000 microns thick in the case of mucous tissue also, it has been difficult to measure biological information only on the superficial tissue such as epitheliums and lamina propria mucosae.

Furthermore, when measuring components of light traveling in straight lines through a living tissue by using optical fibers placed opposite each other, a mechanical raising means i's needed to vertically raise the surface of the living tissue, which not only imposes an extra strain on the living tissue but may cause a pain, and further, it has been difficult to place the end face of each optical fiber in intimate contact with the superficial tissue of the living body stably with constant pressure.

Moreover, since very thin optical fibers need to be brought close to the epidermic layer of the living body in order to precisely place the optical fiber bundles in intimate contact with the living body, the apparatus is complex in construction and takes a cumbersome procedure to assemble, and besides, it has been difficult to form a large number of grooves.

Though a single groove formed in a flat member is placed in intimate contact with the living body in order to raise a portion of the living body, it has been difficult to sufficiently raise the portion of the living body.

Furthermore, since it is difficult to increase the total area of the end face of the optical fibers, it has been difficult to increase the intensity of diffusely reflected light used for measurement.

On the other hand, the second and third prior art methods have had the following problems.

It is known that the depth, d, to which the evanescent wave penetrates is roughly determined by the following equation (1).

[MATHEMATICAL 1]

$$d = \frac{\lambda}{2\pi \times \sqrt{\sin^2\theta - \left(\frac{n_2}{n_1}\right)^2}} \quad (1)$$

Here, $\lambda$ is the wavelength of light, $\theta$ is the angle of incidence, n1 is the refractive index of the crystal, and n2 is the refractive index of the medium placed in contact with the crystal.

For example, when the wavelength of light is 10 microns, the ATR prism is formed from a ZnSe crystal (refractive index of about 2.41), the angle of incidence is 45 degrees, and the surrounding medium is water (refractive index: about 1.0), then the penetration depth, d, can be calculated as d=2.8 microns from the equation (1). If the refractive index of the surrounding medium changes, the seeping depth also changes, as can be seen from the equation (1), but in any case, the change is a few microns at most, which means that information concerning the surface of the living body and its neighborhood can be obtained using the above-described prior ART measuring apparatus.

However, in this case, information concerning the portions of the living body deeper than a few microns is difficult to obtain; in particular, if there is an external disturbing layer such as an impurity or saliva between the apparatus and the analyte, the depth to which the signal penetrates into the living body changes, causing the signal to change.

Accordingly, in the above-described prior art methods which require the ATR prism be pressed against a lip, the contact between the lip and the surface of the prism is not stable and it is difficult to make measurements with high accuracy. Further, if saliva is present between the prism and the lip, for example, the measured value will be greatly affected by the presence of the saliva.

The ATR prism used for the above purpose is formed from an optical crystal such as ZnSe, ZnS, and KrS. Since these materials are very soft and therefore require great care in handling and cleaning, it is difficult to measure many subjects in succession.

In the fourth prior art method, on the other hand, since the laser light is directed into the living tissue, the laser light entering the living tissue is mostly absorbed in the living tissue. If Raman scattered light of the intensity necessary to detect biological information is to be obtained, laser light of great intensity must be shone on the living tissue, but this has involved the problem that a burn may be caused because the laser light is absorbed in the living tissue.

DISCLOSURE OF THE INVENTION

The present invention has been devised to solve the above-enumerated problems, and an object of the invention is to provide a biological information detecting probe that is easy to handle and can easily measure a living tissue with high accuracy while minimizing damage to the living tissue, and also provide a fabrication method for the same, a biological information measuring apparatus, and a biological information measurement method.

To achieve the above object, one aspect of the present invention is a biological information detecting probe characterized by comprising:

pressing means having a recessed portion which is pressed against a living tissue;

detection light emitting means of emitting detection light through one part of said, recessed portion; and detection light entrance means which is provided in another part of said recessed portion, and into which said detection light is introduced, and in that:

said pressing means is formed from a material that has a higher refractive index than said living tissue; and with said pressing, means held pressed against said living tissue, said detection light is introduced into said detection light entrance means after being passed through said-living tissue fitted into said recessed portion.

Another aspect of the present invention is the biological information detecting probe characterized in that the angle formed by a plane containing said one part of said recessed portion through which said detection light is emitted makes, and a plane containing said other part of said recessed portion through which said detection light enters is smaller than 180°.

Still another aspect of the present invention is the biological information detecting probe characterized by comprising:

a living tissue pressing part which is pressed against said living tissue and thereby deforms a portion of said living tissue; and a base part which contacts a portion of said living tissue other than the portion thereof against which said living tissue pressing part is pressed, and in that:

said pressing means is formed extending over said living tissue pressing part and said base part.

Yet still another aspect of the present invention is the biological information detecting probe characterized in that said living tissue pressing part and/or said base part include secretion removing means of removing secretion released from said living tissue, said secretion removing means being located in a portion contacting said living tissue.

Still yet another aspect of the present invention is the biological information detecting probe characterized in that said detection light emitting means is provided in said living tissue pressing part, and said detection light entrance means is provided in said base part.

A further aspect of the present invention is the biological information detecting probe characterized in that said detection light emitting means is provided in said base part, and said detection light entrance means is provided in said living tissue pressing part.

A still further aspect of the present invention is the biological information detecting probe characterized in that said detection light emitting means and/or said detection light entrance means include an optical waveguide.

A yet further aspect of the present invention is the biological information detecting probe characterized in that said optical waveguide has a Y-branch shape or a plate-like-shape.

A still yet further aspect of the present invention is the biological information detecting probe characterized in that said optical waveguide in said detection light emitting means is for receiving external input light, and an end face of said optical waveguide, from which said detection light is not emitted, is formed so as to guide said input light to an end face from which said detection light is emitted.

An additional aspect of the present invention is the biological information detecting probe characterized in that said end face of said optical waveguide from which said detection light is not emitted totally reflects said input light for input into said optical waveguide.

A still additional aspect of the present invention is the biological information detecting probe characterized in that all or part of said end face of said optical waveguide from which said detection light is not emitted has a grating structure, and said grating structure diffracts said input light for input into said optical waveguide.

A yet additional aspect of the present invention is the biological information detecting probe characterized in that said optical waveguide is formed from a material selected from the group consisting at least of germanium, silicon, and diamond.

A still yet additional aspect of the present invention is the biological information detecting probe characterized in that said optical waveguide is surrounded with a cladding material.

A supplementary aspect of the present invention is the biological information detecting probe characterized in that said optical waveguide is surrounded with a cladding material that has a lower refractive index than said optical waveguide.

A still supplementary aspect of the present invention is the biological information detecting probe characterized in that said base part is formed from a silicon material.

A yet supplementary aspect of the present invention is a fabrication method for the biological information detecting probe including the step of forming said detection light emitting means and/or said detection light entrance means by depositing a germanium material.

A still yet supplementary aspect of the present invention is the biological information detecting probe characterized in that said pressing means is formed from a material that has a higher refractive index than said living tissue.

One aspect of the present invention is the biological information detecting probe characterized in that said recessed portion is provided with a first light blocking film for blocking said detection light, said first light blocking film being formed on a part of said recessed portion other than said one part and said other part thereof.

Another aspect of the present invention is the biological information detecting probe characterized in that said recessed portion is substantially in the shape of an inverted triangle in a cross section taken parallel to a light path of said detection light, and a bottom of said recessed portion does not form a face.

Still another aspect of the present invention is the biological information detecting probe characterized in that said recessed portion is formed so as to have a face at its bottom.

Yet still another aspect of the present invention is the biological information detecting probe characterized in that the part on which said first light blocking film is formed is the bottom of said recessed portion.

Still yet another aspect of the present invention is the biological information detecting probe characterized in that a plurality of said recessed portions are provided.

A further aspect of the present invention is the biological information detecting probe characterized by comprising a second light blocking film formed between said plurality of recessed portions.

A still further aspect of the present invention is the biological information detecting probe characterized in that the light path of said detection light is one that is projected from said detection light emitting means at an angle smaller than the angle formed by a straight line joining the bottom of said recessed portion to an edge of another recessed portion adjacent to said recessed portion, said edge being the part thereof nearest to said bottom, and a straight line passing through said edges of said plurality of recessed portions.

A yet further aspect of the present invention is the biological information detecting probe characterized in that said plurality of recessed portions comprise at least two recessed portions having different de A still yet further aspect of the present invention is the biological information detecting probe as characterized in that said pressing means is formed from Si, Ge, SiC, or diamond.

An additional aspect of the present invention is a biological information measuring apparatus characterized by comprising:

the biological information detecting probe as set forth; in any one of the 1st to 15th inventions or the 18th to 25th invenitons;

a light source for said detection light; and analyzing means of analyzing said detection light passed through said living tissue and introduced into said biological information detecting probe, and in that:

said biological information measuring apparatus acquires biological information based on an analysis result obtained from said analyzing means.

A still additional aspect of the present invention is a biological information measuring apparatus characterized by comprising:

the biological information detecting probe;

a light source for said detection light; and analyzing means of analyzing scattered light generated when said detection light is introduced into said living tissue, and in that:

said biological information measuring apparatus acquires biological information based on an analysis result obtained from said analyzing means.

One aspect of the present invention is the biological information measuring apparatus characterized in that said biological information detecting probe depresses said living tissue to a depth not greater than 5 mm.

Another aspect of the present invention is the biological information measuring apparatus characterized in that said biological information detecting probe depresses said living tissue into a substantially curved shape.

Still another aspect of the present invention is the biological information measuring apparatus characterized in that the angle formed by a contact face that contacts and depresses said living tissue, and a line perpendicular to a plane containing said living tissue other than said contact face is not smaller than 90°.

As described above, according to the present invention, a projecting part is provided on the surface that is brought into contact with a subject, and the living body is deformed by pressing the projecting part against it in this condition, light is shone on the living body, and biological information is calculated by detecting the light passed through the living body.

BRIEF DESCRIPTION OF THE DRAWINGS

FIG. 4 is a process diagram showing a fabrication method for a biological information detecting probe according to the same embodiment of the present invention.

FIG. 5 is a schematic drawing showing a biological information detecting probe and an input/output portion according to another embodiment of the present invention.

DESCRIPTION OF THE REFERENCE NUMERALS

Figure 1:
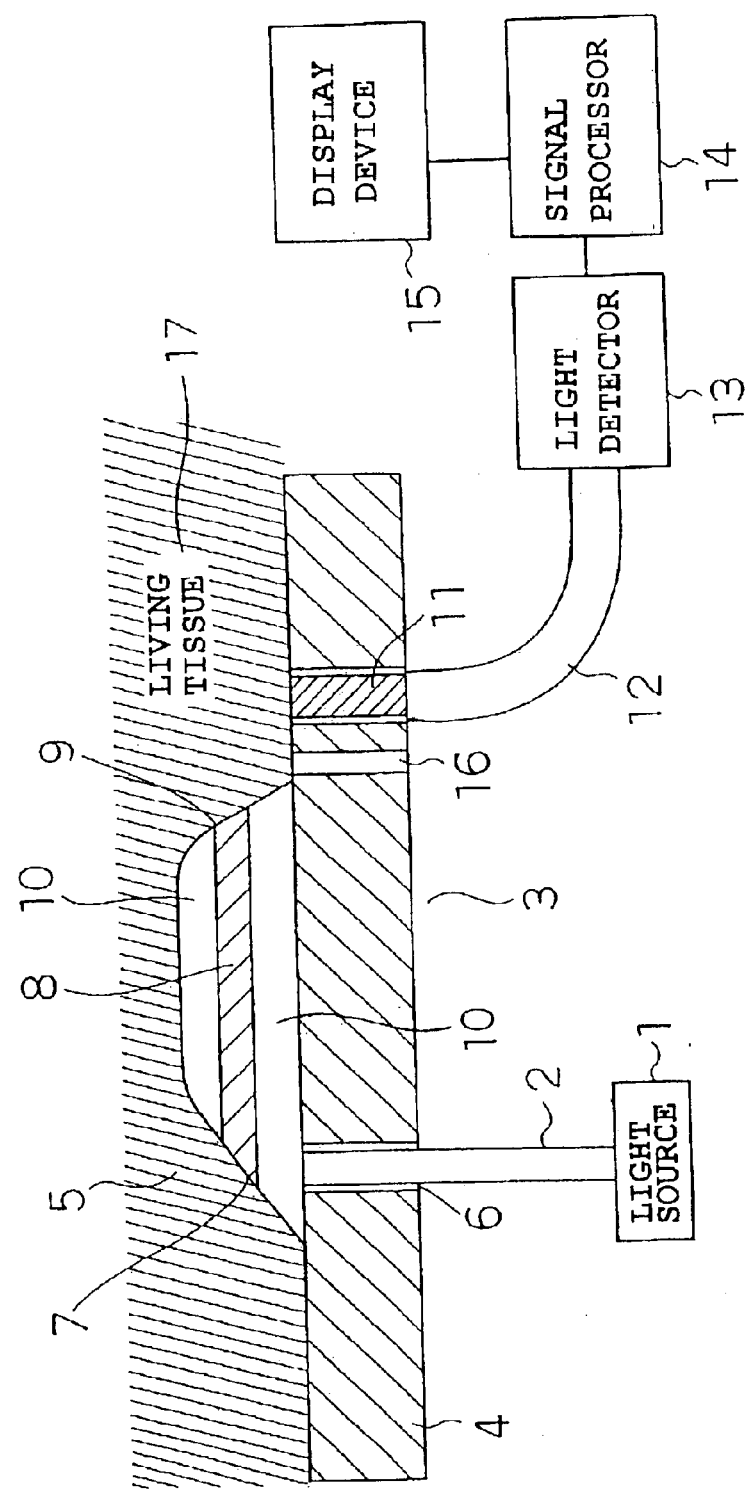
FIG. 1 is a schematic drawing showing, in simplified form, a biological information measuring apparatus according to a first embodiment of the present invention.

1. LIGHT SOURCE
2, 12. OPTICAL FIBER
3. LIGHT SENSOR
4. SUBSTRATE
5. RAISED PORTION
6, 16. HOLE
7. REFLECTING FACE
8. LIGHT EMITTING MEANS
9. EXIT END FACE
10. CLAD LAYER
11. LIGHT RECEIVING MEANS
13. LIGHT DETECTOR
14. SIGNAL PROCESSOR
15. DISPLAY DEVICE
20. ATR PRISM
21. LIP MUCOSA
31. BIOLOGICAL INFORMATION DETECTING PROBE
32, 310, 343. RECESSED PORTION
33, 311, 344. RAISED PORTION
34. LIGHT SOURCE
35. LIGHT DETECTOR
36. SIGNAL PROCESSOR
37. DISPLAY DEVICE
38. LIVING TISSUE
39. INPUT/OUTPUT PORTION
320, 340. SILICON SUBSTRATE
321, 322, 341, 342. OXIDE

BEST MODE FOR CARRYING OUT THE INVENTION

Embodiments of the present invention will be described in detail below with reference to drawings.

A biological information measuring apparatus according to an embodiment of the present invention comprises a light source, a substrate having a raised portion for depressing a surface of a living body, a light emitting means which is provided on the substrate and which emits light produced by the light source onto the surface of the living body, a light receiving means which receives the light emitted from the light emitting means, a detector for detecting the light received by the light receiving means, and a signal processor for calculating biological information using a signal obtained by the detector, wherein either the light emitting means or the light receiving means is disposed in the raised portion formed on the substrate.

In a preferred mode of the biological information measuring apparatus according to the embodiment of the present invention, the light emitting means and the light receiving means are formed from germanium.

(Embodiment 1)

A biological information measuring apparatus according to a first embodiment of the present invention will be described below with reference to FIG. 1. In the figure, reference numeral 1 is a light source, 2 and 12 are optical fibers, 3 is a light sensor, 4 is a substrate, 5 is a raised portion, 6 and 16 are holes, 7 is a reflecting face, 8 is a light emitting means, 9 is an exit end face, 10 is a clad layer, 11 is a light receiving means, 13 is a light detector, 14 is a signal processor, and 15 is a display device.

A high intensity ceramic light source that emits light at wavelengths of 1.3 to 10 microns, for example, is used as the light source 1. A $CO_2$ laser may be used instead. The optical fiber 2 transmits the light emitted from the light source 1 and guides it to the light sensor 3. An infrared optical fiber formed from silver bromide or silver chloride based material, a chalcogenide optical fiber, or an optical fiber of hollow structure is used as the optical fiber here.

The light sensor 3 is placed in intimate contact with the surface of a living body, such as a lip mucosa 21, as shown in the figure, for example, and the raised portion 5 formed on the substrate 4 of the light sensor 3 acts to depress the surface of the living body. The amount of depression is preferably 5 mm or less, but is not specifically limited as long as the light sensor can be brought into intimate contact with the living tissue.

The substrate 4 is formed, for example, from a fluoro resin, reinforced plastic, silicon, or glass.

Forming the raised portion 5 in a curved shape as shown is highly desirable from the standpoint of alleviating the pain inflicted on the living body as well as enhancing the adhesion to it.

The optical fiber 2 is inserted in the hole 6 formed through the substrate 4, and the light guided through the optical fiber 2 is introduced into the raised portion 5.

The reflecting face 7 of the raised portion 5 is not specifically limited in shape, but preferably it is shaped so as to provide an angle at which the light reaching it is totally reflected.

Though not shown here, it is also preferable to provide a grating so that the light from the light source is introduced into the light emitting means 8.

Also preferably, the light emitting means 8 is surrounded with the clad layer 10 which protects the light emitting means 8 and also acts as an optical buffer layer to prevent seeping light from the light emitting means 8 from being attenuated by contacting a highly absorbent substance.

The material for the light emitting means 8 should be transparent to radiation in the wavelength region used; for example, germanium, silicon, diamond, and silver bromide or silver chloride based materials are preferred for use. Silicon not doped with impurities such as phosphorus or boron is further preferred because transparency at the infrared band is then enhanced. The light emitting means 8 is shown in the figure as being formed in a plate-like shape, but it may be formed in a Y-branch shape.

A material relatively transparent at the light wavelengths in the infrared region and having a refractive index smaller than that of the light emitting means 8 is used for the clad layer 10. For example, a fluoro resin is a preferred material; when the light emitting means 8 is formed from germanium, silicon is also preferred.

Preferably, the substrate 4 is constructed, for example, from a silicon or glass substrate or a substrate made of heat resistant resin, and silicon as the clad layer and germanium as the light emitting means are deposited on the substrate 4 by using a film deposition process such as sputtering or electron beam deposition.

It is preferable that the exit end face 9 of the light emitting means 8 be not formed vertical, because it would then impair adhesion to the living tissue, but be formed somewhat slanted as shown in the present embodiment.

The operation of the biological information measuring apparatus of the present embodiment having the above configuration will be described below.

The light emitted from the light source land introduced through the optical fiber 2 and the clad layer 10 into the raised portion 5 is reflected by the reflecting face 7 formed on the side face of the raised portion 5, and is input into the light emitting means 8.

The light input into the light emitting means 8 is guided therethrough and emitted through the exit end face 9 into the living tissue 17.

Next, the propagation path of the light emitted through the exit end face 9 will be briefly described below.

Figure 2:
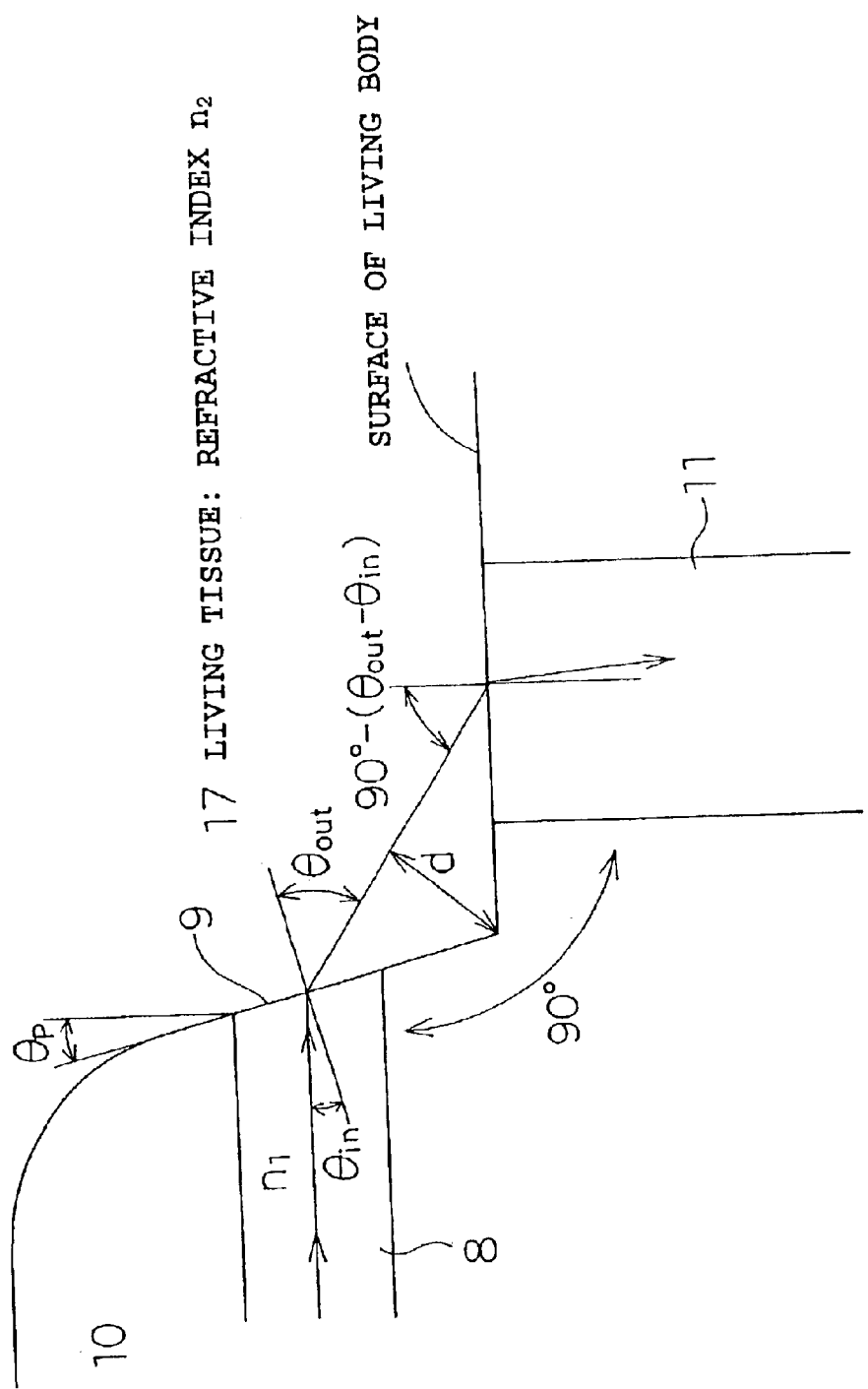
FIG. 2 is a diagram for explaining a light propagating path in a biological information measuring apparatus according to a second embodiment of the present invention.

Referring to FIG. 2, an explanation will be given of how the light propagating in straight lines through the center of the light emitting means 8 travels when the angle of the exit end face 9 is 15 degrees relative to the normal to the substrate 4.

The following explanation is given by taking as an example the case where the light emitting means 8 is formed from germanium with a refractive index $n_1=4.0$, and the refractive index $n_2$ of the living tissue 17 is 1.5.

Assuming that the light propagating in straight lines through the center of the light emitting means 8 is incident at an incidence angle θ in on the extend face 9, the incident light emerges at an emergence angle θ out to enter the living tissue 17 in accordance with Snell's equation given below.

$$n_1 \times \sin(\theta\ in) = n_2 \times \sin(\theta\ out) \quad \text{[MATHEMATICAL 2]}$$

Substituting the above values in this equation, the emergence angle θout is calculated as 43.6 degrees; therefore, the light emitted from the light emitting means 8 is refracted toward the bottom in the figure as it enters the living tissue 17. The light entering the living tissue 17 travels therethrough while being partially scattered, and reaches the light receiving means 11.

Assuming that the angle that the longitudinal direction of the light emitting means 8 makes with the longitudinal direction of the light receiving means 11 is 90 degrees, the light passed through the living tissue 17 is incident at an incidence angle (90 degrees−(θout−θin)) on the light receiving means 11. Substituting the above values, the concrete incidence angle is calculated as 61.4 degrees. The light is refracted as it enters the light receiving means 11. If the light receiving means 11 is also formed from germanium, the light enters at an angle of 19.2 degrees according to Snell's equation given above, and propagates through the light receiving means 11.

In this way, in the present embodiment, since germanium having a relatively high refractive index is used for the light emitting means 8, the refraction angle when the light enters the living tissue 17 is very large; as a result, there is no need to position the light receiving means 11 directly opposite the light emitting means 8, and the light can be received by the light receiving means 11 whose position is different by 90 degrees axis to that of the light receiving means 11, as shown in FIG. 1. This feature is extremely useful because, by just depressing the surface of the living body into an extremely gently curved shape, the living tissue can be measured while maintaining good adhesion to it and without hurting the living body.

The above description has been given by dealing with the light traveling in straight lines through the light emitting means 8, but some of the light travels in zigzag lines through the light emitting means 8. The above principle also holds for the case of such zigzagging light, and the part of the light emitted through the exit end face 9 can be made to reach the light receiving means 11.

Next, the operation of the present embodiment will be described. The light entering the light receiving means 11 is transmitted through the optical fiber 12 and reaches the light detector 13 which performs various kinds of spectrum analyses including conversion into an electrical signal for each wavelength component.

When the concentration of an absorbing substance in the living tissue 17 changes, signal strength at a particular wavelength also changes; therefore, by measuring the signal strength, biological information such as the concentration of glucose can be calculated in the signal processor 14. The biological information thus calculated is displayed on the display device 15.

The hole 16 formed through the substrate 4 serves to remove impurities such as saliva present between the living tissue and the optical sensor 3. This enhances the adhesion between the living tissue and the light sensor, and allows highly accurate measurements of biological information by preventing the attenuation of light and changes in characteristics that can occur when the light is transmitted through impurities.

Thus, the biological information measuring apparatus according to the present embodiment offers a great advantage because, when the invention is applied, not only can biological information be measured while maintaining good contact between the light sensor and the surface of the living body, but the distance between the light exit end face 9 and the light incident face of the light receiving means 11 can be set at any suitable value according to the design requirement.

This serves to greatly improve the seeping depth of a few microns of the seeping light called the evanescent wave, which, in the prior art ATR method, is determined by the refractive index of the prism material and the refractive index at the surface of the living body; this not only makes it easy to measure the portions of the living body deeper than a few microns, but the path length of the light propagating through the living body can also be increased easily, so that the optical characteristics of any particular component in the living body even if it is very minute, can be also measured easily.

It is preferable to make the light sensor 3 detachable from the light source 1 and light detector 13 or from the optical fibers 2 and 12, since it can then be easily replaced when the surface of the light sensor is soiled or scratched after measuring biological information.

The biological information detecting probe of the present invention corresponds to the structure comprising the substrate 4, raised portion 5, light emitting means 8, clad layer 10, and light receiving means 11 in the present embodiment, and the secretion removing means of the present invention corresponds to the hole 16 in the present embodiment. The living tissue pressing part of the present invention corresponds to the raised portion 5 in the present embodiment, and the base part of the present invention corresponds to the substrate 4 in the present embodiment, which, together with the exit end face 9 and the light receiving means 11, constitute the pressing means of the present invention. The optical waveguide in the detection light emitting means of the present invention corresponds to the light emitting means 8 in the present embodiment, and in the detection light entrance means of the present invention corresponds to the light receiving means 11 in the present embodiment. The light source of the present invention corresponds to the light source 1 and optical fiber 2 in the first embodiment, and the analyzing means of the present invention corresponds to the structure comprising the optical fiber 12, light detector 13, signal processor 14, and display device 15 in the present embodiment.

The above embodiment has been described assuming that the living tissue 17 is placed in intimate contact with the clad layer 10 and the substrate 4, but the pressing means of the present invention is not limited to this particular structure; for example, the structure may be such that the living tissue is fitted in a recessed portion, the only requirement being that the living tissue be placed in contact with one part of the recessed portion through which detection light exits and with another part thereof into which the emitted detection light is introduced. For example, in the present embodiment, if the living tissue 17 is placed in contact with at least the exit end face 9 and the light receiving means 11, the same effect as described above can be obtained even if other portions of the living tissue 17 are not in contact with the substrate 4 or the recessed portion 5 in the vicinity of the hole 16.

(Embodiment 2)

Figure 3:
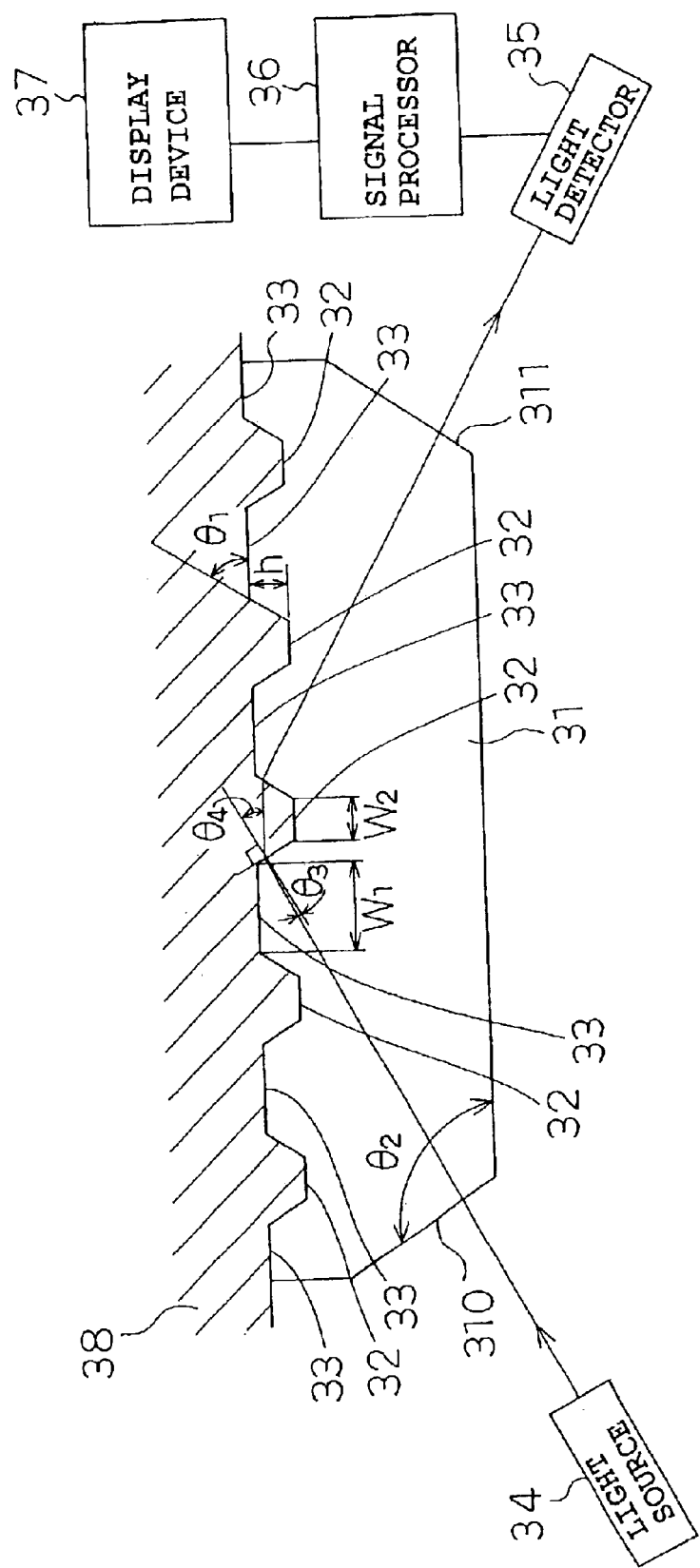
FIG. 3 is a schematic drawing showing the configuration of a biological information measuring apparatus according to one embodiment of the present invention.

A second embodiment of the present invention will be described below with reference to FIG. 3. FIG. 3 is a schematic diagram showing a biological information measuring apparatus according to the second embodiment of the present invention.

A biological information detecting probe 31 is constructed using, for example, a silicon single-crystal substrate transparent at wavelengths of 1.1 to 10 microns. A material whose content of impurities such as boron and phosphorus is low, and whose resistivity is not smaller than 100 Ωcm, is particularly preferable. A material with resistivity not smaller than 1500 Ωcm is more preferable. Such high resistivity silicon has high transmittance at infrared wavelengths of about 9 to 10 microns, and is preferred when measuring glucose or other substances that have absorption regions in this wavelength band.

A plurality of recessed portions 32 and raised portions 33, each formed in a trapezoidal shape having the same depth h, are formed in periodically repeating fashion on the surface of the biological information detecting probe 31. These recessed portions 32 and raised portions 33 serve to deform the living tissue 38 when the biological information detecting probe 31 is pressed against the living tissue 38.

The depth h of the recessed portions 32 is not specifically limited, but when itis set to about 100 microns, biological information mainly concerning the epidermis can be measured because the raised portions 33 are pressed only into the epidermis of the living tissue 38. When it is set to about 200 microns, on the other hand, biological information concerning the dermis as well as the epidermis can be detected. In this way, by adjusting the depth h of the recessed portions 32, the depth in the living tissue 38 at which the measurement is to be taken can be easily controlled. In the present embodiment, h is set to 100 microns.

The top width $W_1$ of the raised portions 33 is not specifically limited, but if the width is too large, it becomes difficult to press the raised portions 33 into the living tissue 38; therefore, it is preferable to set the width to 1 mm or less. In the present embodiment, $W_1$ is set to 100 microns.

The bottom width $W_2$ of the recessed portions 32 is not specifically limited, but if the width is too small compared with $W_1$, it becomes difficult to press the raised portions 33 into the living tissue 38; therefore, it is preferable that $W_2$ be set not smaller than $W_1$. $W_2$ is a parameter that determines the path length of the light propagating through the living tissue 38, and when making measurements in the infrared wavelength region where absorption by water is particularly large, if $W_2$ is too large, light is absorbed and the transmittance drops significantly. For example, at wavelengths longer than about 39 microns, light is substantially absorbed by water; therefore, it is preferable that $W_2$ be set to 300 microns or less. More preferably, $W_2$ should be set to 200 microns or less. In the present embodiment, $W_2$ is set to 100 microns.

The side slope angle $\theta_1$ of the recessed portions 32 is not specifically limited, but if it is close to 90 degrees, it becomes difficult to press them into contact with the living tissue 38; therefore, it is preferable that the angle be set smaller. In the present embodiment, $e_1$ is set to 54.7 degrees.

The portion 310 where detection light enters the biological information detecting probe 31 and the portion 311 where the detection light exits the biological information detecting probe 31 are each formed slantingly relative to the surface of the biological information detecting probe 31, as shown in FIG. 3, so that the light can enter and exit without undergoing total reflection in the biological information detecting probe 31. In the and thus, the light can be made to enter and exit the 24 biological information detecting probe 31 efficiently. In the present embodiment, the slope angle $\theta_2$ of each of the detection light entrance portion 310 and exit portion 311 is set to 111.6 degrees.

A fabrication method for the biological information detecting probe 31 according to the present embodiment will be described below with reference to FIG. 4.

Anisotropic wet etching was used for the fabrication of the biological information detecting probe 31 made of single-crystal silicon. This method is chemical etching that uses an aqueous solution of KOH or an aqueous solution of ethylenediamine, and utilizes the property that the etching rate along the (111) direction of single-crystal silicon is extremely low compared with that along any other direction.

First, as shown in FIG. 4(a), oxide films 321 and 322 are formed as protective layers on the upper and lower surfaces of the single-crystal silicon substrate 320.

Next, the oxide film 321 is patterned in the desired shape, as shown in FIG. 4(b).

After that, the silicon substrate 320 is immersed, for example, in a 40% solution of KOH for etching. When the silicon wafer whose (100) crystal plane is oriented along the direction of the normal to the surface is etched, recessed portions 32 whose side faces are slanted at an angle of 54.7 degrees are formed as shown in FIG. 4(c). After forming the recessed portions 32, the oxide film 321 is removed, resulting in the formation of raised portions 33 between the recessed portions 32, as shown in FIG. 4(d). Here, the protective layers may be formed using silicon nitride films.

The above has described the method that forms the recessed portions 32 by anisotropic wet etching of the silicon single-crystal substrate, but instead, ultrasonic machining may be used.

Ultrasonic machining is a machining method that grinds material by abrasive grit; in this method, while applying vibrations of a frequency of 20 kilohertz and an amplitude of 30 microns or larger to a tool having the shape corresponding to the finished shape, abrasive grit such as boron carbide is supplied in a slurry and the tool is pressed against the workpiece to be machined.

The entrance portion 310 and exit portion 311 on the back of the biological information detecting probe 31 of the present invention can also be formed using the same method as described above.

Next, the principle of operation of the biological information measuring apparatus of the present invention will be described below with reference to FIG. 3.

Part of the light emitted from the light source 34 and introduced into the biological information detecting probe 31 through the incident portion 310 reaches a side face of a recessed portion 32. The incidence angle of the detection light on the slanted face of the recessed portion 32 is set so that, of the light entering the living tissue 38, rectilinearly propagating components again reach the recessed portion 32, by considering the refractive index of the living tissue 38, the refractive index of the biological information detecting probe 31, and the angle of the side face of the recessed portion 32. Preferably, the incidence angle is set so that when the living tissue 38 is placed in contact with the recessed portion 32, the light travels through the living tissue 38 horizontally in the figure.

For example, when the side face of the recessed portion 32 is slanted at an angle of 54.7 degrees, and when the refractive index of the living tissue 38 is $n_2=1.4$ and that of the silicon forming the biological information detecting probe 31 is $n_1=3.418$, the light is to incident on the slanted face of the recessed portion 32 at an angle $\theta_3=13.7$ degrees. Since the biological information detecting probe 31 of the present embodiment is constructed using silicon which is a substance of high refractive index, the difference from the refractive index of the living tissue 38 is large; as a result, by tilting the incident light by the small angle $\theta_3$ relative to the slanted face of the recessed portion 32, the detection light can be refracted at a large angle, and thus the refraction angle $\theta_4$ at which the light enters the living tissue 38 can be made large.

The refraction angle $\theta_4$ can be calculated by Snell's equation (equation 3) given below.

$$n_1 \times \sin\theta_3 = n_2 \times \sin\theta_4 \qquad \text{[MATHEMATICAL 3]}$$

From equation 3, $\theta_{4=35.3}$ degrees. Refracting the light by $\theta_4=35.3$ degrees relative to the slanted face of the recessed portion 32 means that the light is deflected into a substantially horizontal direction in FIG. 3.

It is generally known that light propagating through a living body is scattered and diffused, but when the method of, the invention is used, rectilinearly propagating light having the highest intensity can be received at the side face of the other raised portion located on the opposite side.

The detection light passed through the living tissue 38 enters the biological information detecting probe 31 by being refracted at the face where it exits the living tissue 38, just as it was refracted when entering the living tissue 38. After that, the detection light is emitted outside the biological information detecting probe 31 and detected by the light detector 35. Based on the detection result from the light detector 35, biological information is calculated in the signal processor 36, and the result is displayed on the display device 37.

The light detected by the light detector 35 contains many light components passed through the interior of the living tissue 38, especially, the superficial tissue, but less components carrying biological information from deeper portions of the living body such as subcutaneous fatty tissue; therefore, by analyzing the spectrum of the detected light, biological information concerning the target layer in the living tissue can be measured easily and with high sensitivity.

There are cases where good contact cannot be obtained between the recessed portion 32 of the biological information detecting probe 31 and the living tissue 38 at the lower end of the side face of the recessed portion 32.

However, in many of such cases, air exists in the gap created between the living tissue 38 and the side face of the recessed portion 32. Since the refractive index of air is n=1.0, the difference from the refractive index of the biological information detecting probe 31 is greater than the difference from that of the living tissue, which means that, in this air gap, the light is refracted at a larger angle than the light passing through the contacted living tissue 38, and therefore, is directed away from the normal light path.

As a result, unwanted light that does not contain biological information exits the biological information detecting probe 31 at a different angle, and such light is therefore not detected by the light detector 35, that is, unwanted light is eliminated, and biological information can thus be calculated correctly.

(Embodiment 3)

A third embodiment of the present invention will be described below with reference to FIG. 5. FIG. 5 is a schematic diagram showing a biological information detecting probe according to the third embodiment of the present invention.

The biological information detecting probe 31 is constructed using a silicon single-crystal substrate, the same material as that used in the second embodiment. A plurality of recessed portions 32 and raised portions 33, each formed in a triangular shape having the same depth h, are formed in periodically repeating fashion on the surface of the biological information detecting probe 31. These recessed portions 32 and raised portions 33 serve to deform the living tissue 38 when the biological information detecting probe 31 is pressed against the living tissue 38. In the present embodiment, h=100 microns. The side slope angle $\theta_1$ of the recessed portions 32 is set to 31.5 degrees.

An input/output portion 39 made of Ge is formed on the back of the biological information detecting probe 31. The portion where detection light enters the input/output portion 39 and the portion where the detection light exits the input/output portion 39 are each formed slantingly relative to the interface between the biological information detecting probe 31 and the input/output portion 39, as shown in FIG. 5, so that the light can enter and exit without undergoing total reflection in the input/output section 39. In the present embodiment, the slope angle $\theta_2$ of each of the detection light entrance portion 310 and exit portion 311 is set to 138.6 degrees.

A fabrication method for the biological information detecting probe 31 according to the present embodiment will be described below with reference to FIGS. 6(a) to 6(d)

Figure 6:
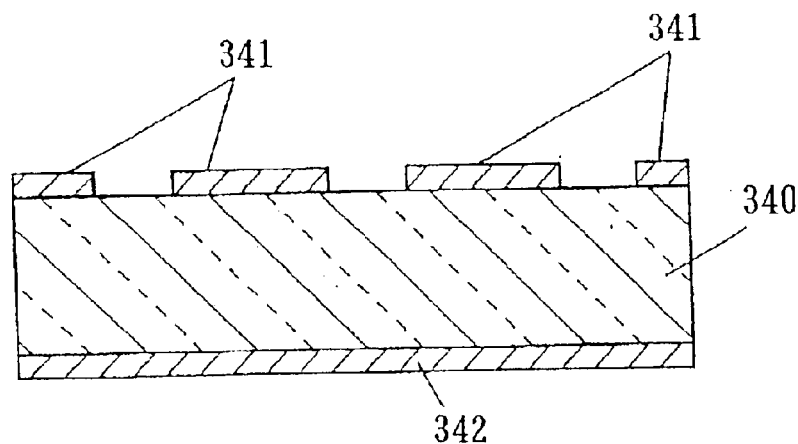
FIG. 6 is a process diagram showing a fabrication method for the biological information detecting probe according to the same embodiment of the present invention.
Figure 6:
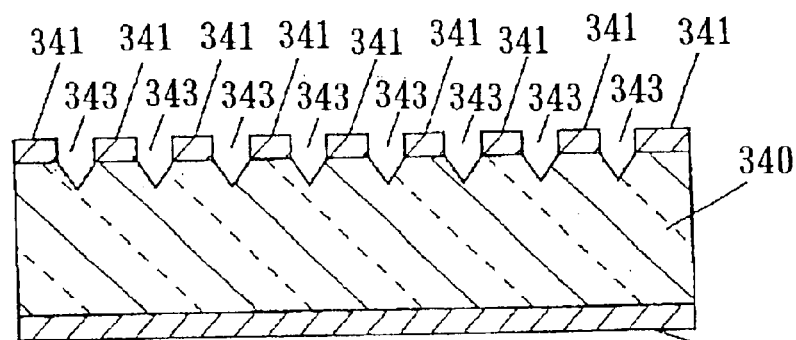
Figure 6:
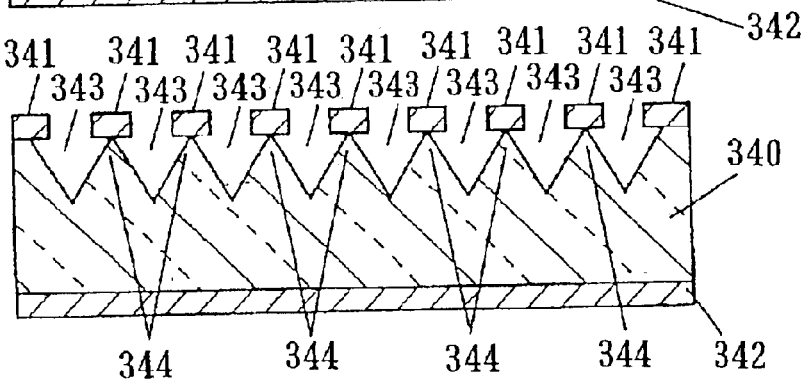
Figure 6:
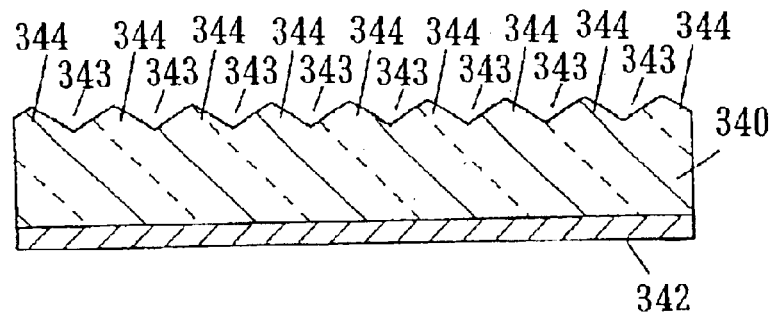

As in the second embodiment, after forming oxide films 341 and 342 on the upper and lower surfaces of the silicon single-crystal substrate 340, a desired pattern is formed as shown in FIG. 6(a).

Next, the silicon substrate 340 is immersed, for example, in a 40% solution of KOH for etching. When the silicon wafer whose (100) crystal plane is oriented along the direction of the normal to the surface is etched, raised portions 344 and recessed portions 343 (V grooves) whose side faces are slanted at an angle of 54.7 degrees are formed as shown in FIG. 6(b). When etching is continued after the V grooves are formed, the (111) crystal plane is gradually etched, and the V grooves widen and grow, as shown in FIG. 6(c).

When etching is further continued, the oxide film 341 remaining on the vertex of each raised portion 344 is removed, and the (100) crystal plane at the vertex is etched. Since the (100) crystal plane is etched at a faster rate than the (111) crystal plane, the vertex is etched and the height decreases gradually as the time elapses, and when the etching is stopped at a particular point in time, for example, V grooves formed by the (311) crystal plane result, as shown in FIG. 6(d).

The back surface of the biological information detecting probe of the present invention can also be processed using the same method as used in the second or third embodiment.

The bonding between the biological information detecting probe 31 and the input/output portion 39 can be accomplished, for example, by polishing the contact faces smooth and joining them together using interatomic forces acting between them.

Alternatively, pressure may be applied by holding them in contact with each other. Any suitable method may be used as long as the light can be propagated from the input/output portion 39 to the biological information detecting probe 31 and vice versa without causing total reflection at the interface.

When the biological information detecting probe 31 of the present embodiment is used in a biological information measuring apparatus similar to the one of the second embodiment, biological information concerning the target layer in the living tissue can be measured easily and with high sensitivity, as in the second embodiment.

The biological information detecting probe 31 of the present embodiment provides a large contact angle of 117 degrees and thus ensures very smooth contact with the living tissue 38. Therefore, when the biological information detecting probe 31 is pressed against the living tissue 38, not only can the raised portions 33 of the biological information detecting probe 31 be easily pressed into the living tissue 38, but the living tissue 38 can also be easily made to contact the side faces of the recessed portions 32 firmly. Furthermore, since the area of the contact surface with the living tissue 38 is increased, much of the detection light can be introduced into the living tissue 38, eliminating the need to collect light using expensive lenses.

(Embodiment 4)

Figure 7:
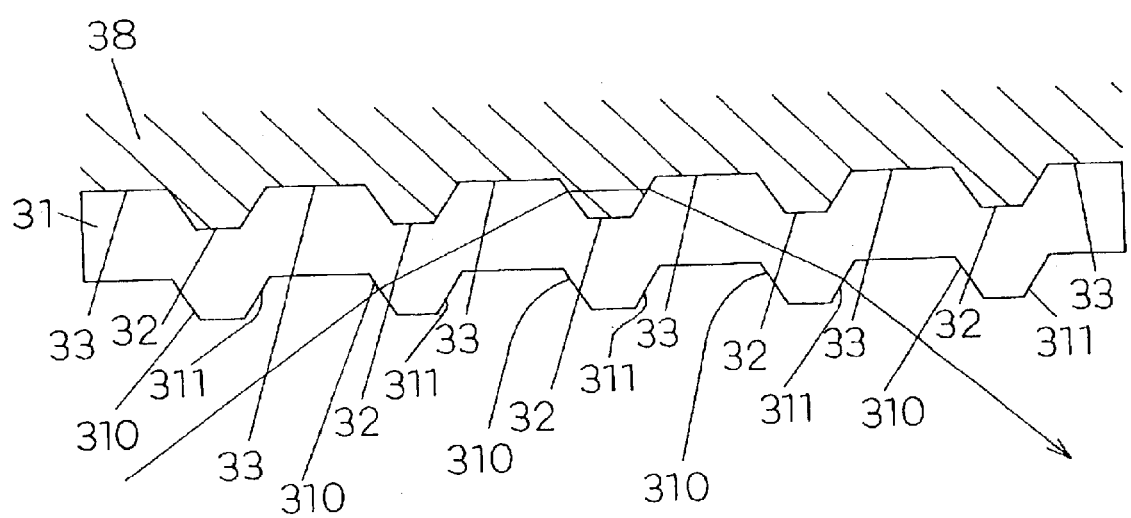
FIG. 7 is a schematic drawing showing a biological information detecting probe according to a further embodiment of the present invention.

A fourth embodiment of the present invention will be described with reference to FIG. 7. FIG. 7 is a schematic diagram showing a biological information detecting probe according to the fourth embodiment of the present invention.

As in the second embodiment, a single-crystal silicon substrate is anisotropically etched to form recessed portions 32 with side faces slanted at an angle of 54.7 degrees, but the difference from the second embodiment is that a periodic pattern of recessed portions 310 and raised portions 311 is also formed on the back surface of the single-crystal silicon substrate, in which the side faces of the recessed portions 310 and raised portions 311 serve as the detection light entrance portion 310 and exit portion 311.

The side slope angle of each recessed portion 310 should be set at such an angle that does not cause total reflection of the detection light, and an angle of about 80 degrees is preferable; such recessed portions can be easily formed using an ultrasonic-machining method.

Light reaching the side face of a raised portion 310 on the back surface of the biological information detecting probe 31 propagates in a straight line through the inside of the biological information detecting probe 31, and reaches the side face of a recessed portion 32 formed on the side of the probe that contacts the living body. After that, the light is refracted at a large angle because of the difference in refractive index between the living tissue and the biological information detecting probe, passes through the superficial tissue of the living body, and again reaches the side face of the recessed portion 32, at which the light is refracted in the direction of the raised portion 311 formed on the back surface. Since at the position the refracted light reaches, the side face of the raised portion 311 is set, the light is passed therethrough without total reflection and is emitted outside. When compared with the configuration example shown in FIG. 8(b) to be described later, the above-described structure can reduce the thickness, size, and weight of the biological information detecting probe 31 in a configuration where a plurality of light sources are provided.

When the biological information detecting probe 31 of the present embodiment is used in a biological information measuring apparatus similar to the one of the second embodiment, biological information concerning the target layer in the living tissue can be measured easily and with high sensitivity, as in the second embodiment.

The above embodiment has been described by dealing with the case where the detection light entering the biological information detecting probe after passing through the living tissue is analyzed, but alternatively, biological information may be obtained by using laser light, such as that generated by an argon laser, a YAG laser, or a semiconductor laser, as detection light, and by analyzing the scattered light generated when the detection light propagates through the living tissue. When the biological information detecting probe of the present invention is used, much of the detection light introduced into the living tissue can be fed back to the biological information detecting probe; as a result, even when high intensity laser light is used, damage to the living tissue can be reduced, and the problem of burning caused by the projection of the detection light can be eliminated.

Figure 8:
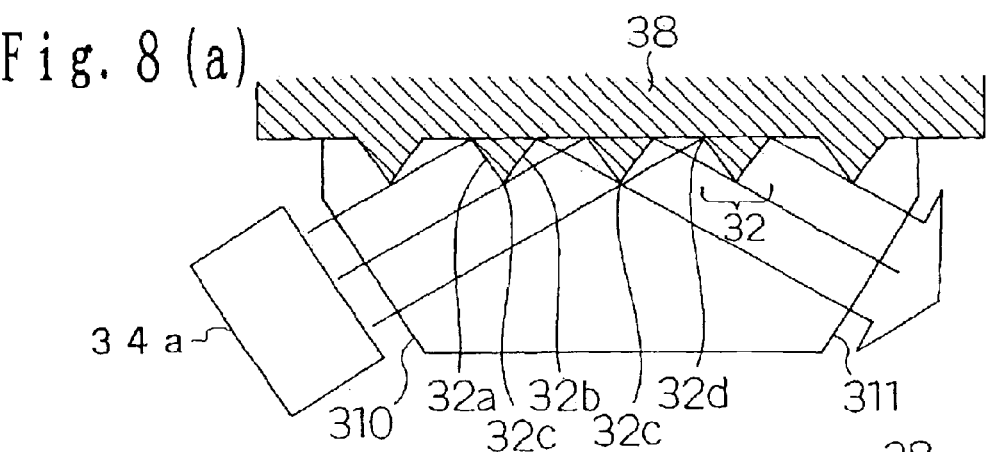
FIG. 8 is a schematic drawing showing configuration examples of a biological information detecting probe according to a further embodiment of the present invention.
Figure 8:
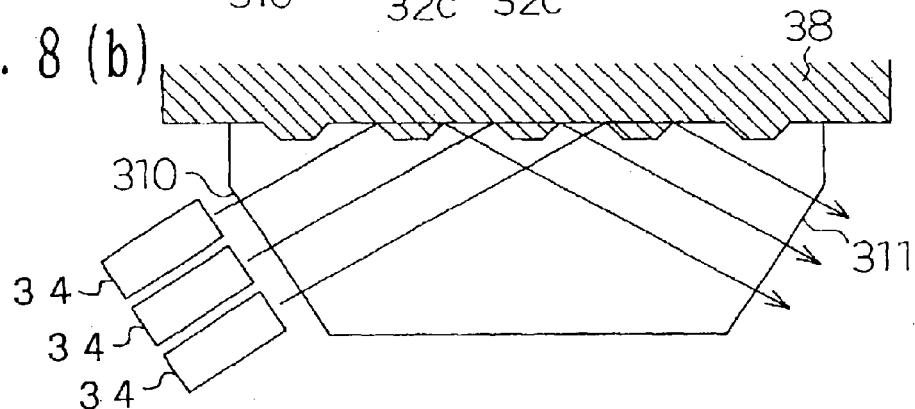
Figure 8:
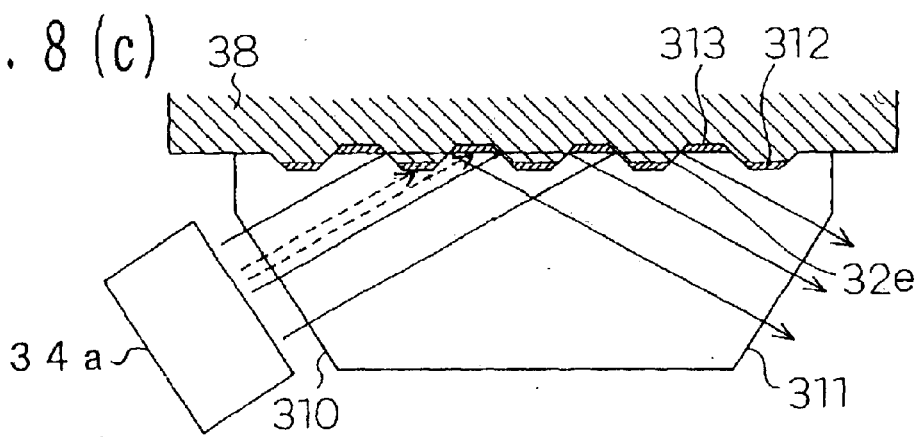
Figure 8:
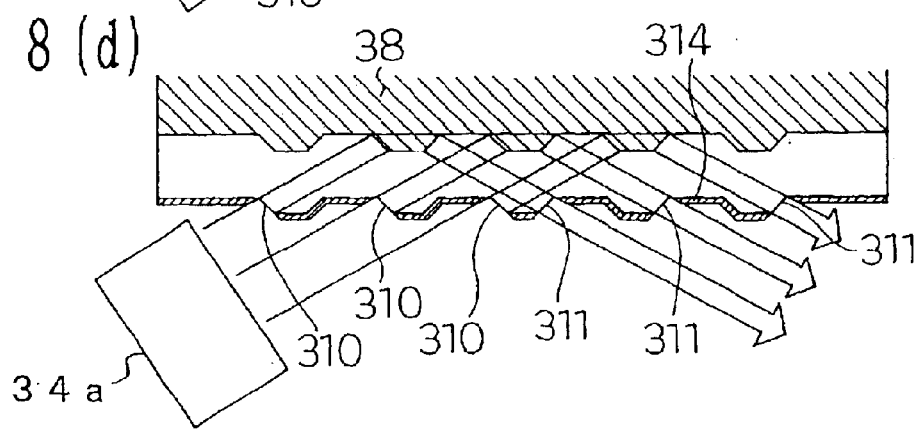

Next, FIGS. 8(a) to 8(c) show other configuration examples of the biological information detecting probe according to the second to fourth embodiments. FIG. 8(a) shows an example in which the recessed portions 32 are each formed in the shape of a V groove in a cross section taken parallel to the light path of the detection light. As shown, the cross section of each recessed portion 32 consists only of side faces 32a and 32b, and has a pointed bottom 32c which does not have a width corresponding to the wide $W_2$ in the above embodiment.

In this example, all of the detection light from the light source enters through the side faces 32a of the recessed portions 32, is passed through the living tissue 18, and exits from the side faces 32b.

According to this configuration example, since there are no unwanted light components in the light emitted from the light source 4, a wide light source 34a that can produce wider light than the light source of the above embodiment can be used more efficiently as detection light.

In order for all of the detection light to enter through the side faces 32a, the incidence angle of the incident light should be made smaller than the angle formed by a straight line joining the bottom 32c to an edge 32d of a recessed portion 32 located adjacent to the recessed portion 32 having that bottom 32c, and a straight line joining a plurality of edges 32d. With this setting, the detection light emitted from the light source can be prevented from entering the living tissue 38 through the raised portions 33, not through the recessed portions 32.

FIG. 8(b) shows a configuration example in which a plurality of light sources 34 are provided. In this configuration, since detection light emitted from each individual light source can be detected independently of the others, more accurate values can be obtained based on the detection results of individual detection light.

FIG. 8(c) shows an example in which a light blocking film 312 is formed on the bottom 32e of each recessed portion 32 and a light blocking film 313 on the top of each raised portion 32. The light blocking film 313 serves to prevent the detection light from passing through the top of the raised portion 33 and entering the living tissue 32, and also prevent light reflected from the light blocking film 313 from exiting from the exit face 311. On the other hand, the light blocking film 312 serves to prevent the detection light from entering through the bottom 32e, and also prevent light from being reflected at the bottom 32e and exiting from the exit face 311.

FIG. 8(d) shows an alternative configuration example of the fourth embodiment, in which light blocking films 314 are formed on the bottoms of the recessed portions 310 and raised portions 311 formed in periodically repeating fashion on the back surface of the silicon single-crystal substrate. With this configuration, a light source that can produce wide laser light, such as the wide light source 34a shown in the configuration example of FIG. 8(a), can be used to generate detection light.

In the above description, it is desirable that the light blocking films 312 to 314 be each provided with a light absorbing or antireflection function.

The biological information detecting probe of each of the above embodiments can be used by placing it in direct contact with a finger, lip, arm, earlobe, or other part of a living body, but when measuring biological information by placing the biological information detecting probe in contact with a lip, saliva may be trapped between them. It is therefore preferable that a hole, a deep groove, or like means for removing the saliva trapped between the living body and the biological information detecting probe, though not shown here, be formed in the bottom of the recessed portion of the biological information detecting probe.

Further, when light is incident on a portion other than the side faces of the recessed portions of the biological information detecting probe, that is, when light is incident on the top of a raised portion or the bottom of a recessed portion, much of the light is totally reflected, and may be emitted from the biological information detecting probe and reach the detector. Since such light does not contain biological information, it is not preferable to detect such light together with light containing biological information. It is therefore preferable that light absorbing means, such as the light blocking films 312 to 314 described above, be formed on the top of each raised portion or the bottom of each recessed portion.

Any absorbing means may be used as long as it can absorb light at the wavelengths used; for example, when the detection light has wavelengths of 9 to 10 microns, use can be made of an oxide film such as a silicon dioxide film or a titanium dioxide film, or a nitride film such as a silicon nitride film. It is preferable that a multilayer film consisting of such material and silver or tungsten silicide be formed to further enhance the absorbing ability by using the interference effect of light.

Each of the above embodiments has been described for the case where the recessed portions and raised portions are all formed with the same height, but instead, recessed portions and raised portions with different heights may be formed. In that case, since the superficial tissue of a living body is pressed to various depths, information in the depth direction can be obtained at a time by detecting information concerning the epidermis with a shallow recessed portion and biological information concerning the dermis with a deep recessed portion at the same time.

Figure 9:
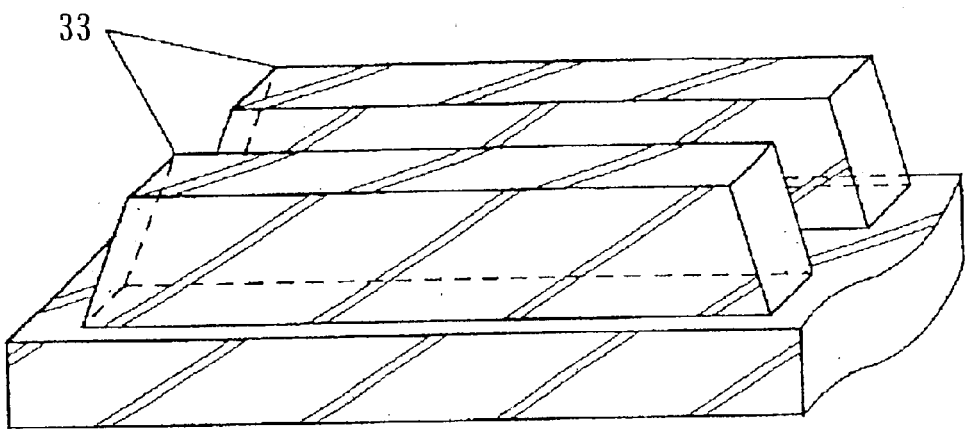
FIG. 9 is a perspective view showing the shape of a raised portion of a biological information detecting probe according to one embodiment of the present invention.

The shape of the biological information detecting probe in the depth direction is not specifically limited, but the raised portions 33 may be elongated in one particular direction as shown in FIG. 9 By so forming, biological information can be detected by pressing the longitudinally elongated raised portions 33 into the living tissue and passing light through each recessed portion. Since longitudinally elongating the raised portions has the effect of increasing the contact area with the living body, the area of the beam passing through the superficial tissue can be increased; this offers the effect of being able to improve the S/N of the detection light.

Figure 10:
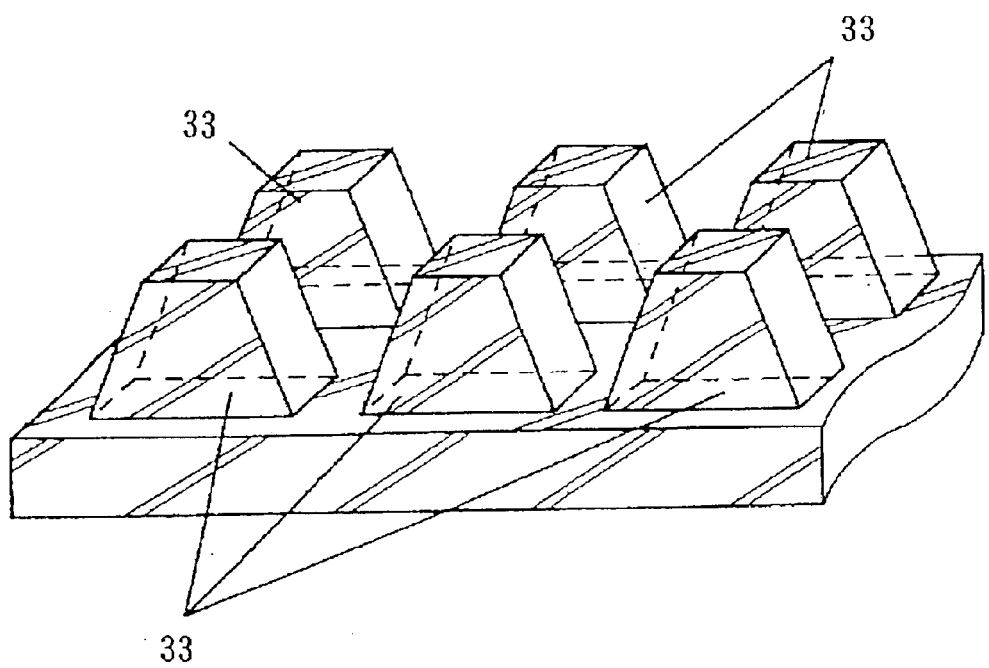
FIG. 10 is a perspective view showing the shape of a raised portion of a biological information detecting probe according to another embodiment of the present invention.
Figure 11:
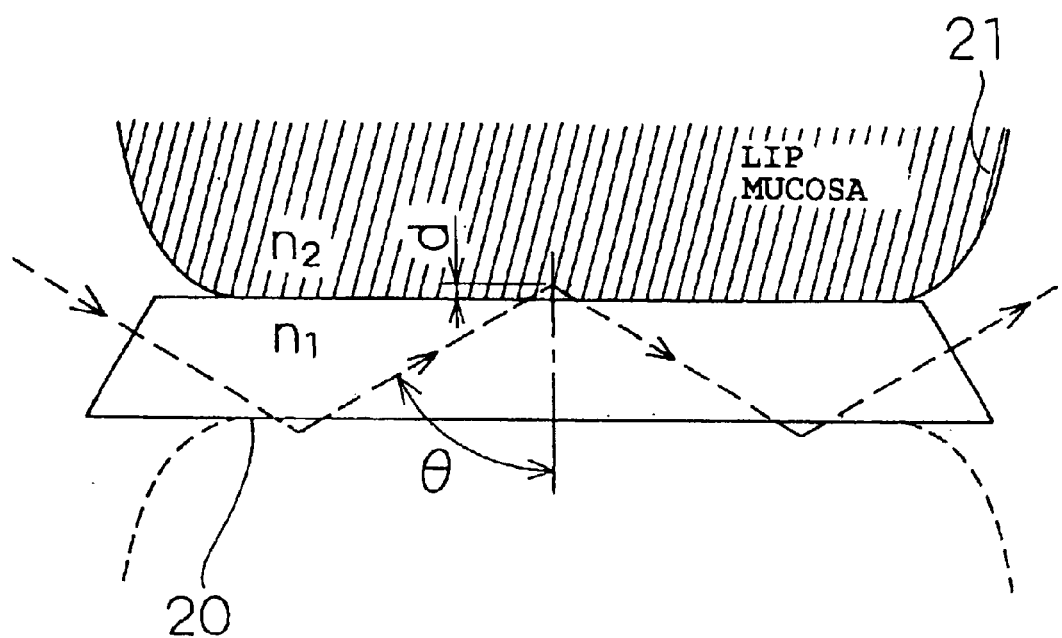
FIG. 11 is a schematic diagram showing one example of a prior art biological information measuring apparatus.

Further, as shown in FIG. 10, the raised portions 33 may be arranged in a two dimensional array. By so arranging, the raised portions can be easily pressed into the living tissue, offering the effect of enhancing the adhesion to the living body and ensuring stable measurement portions can be easily pressed into the living tissue, offering the effect of enhancing the adhesion to the living body and ensuring stable measurement.

As described above, in one example, the biological information detecting probe of the present invention is characterized by comprising a recessed portion which is brought into intimate contact with a living tissue, and in that the recessed portion is formed so that light emitted from one side face of the recessed portion again enters the recessed portion from the other side face thereof after passing through the living tissue, and in that the biological information detecting probe is formed from a material having a higher refractive index than the living tissue.

Preferably, the biological information detecting probe comprises a plurality of such recessed portions.

Also preferably, the biological information detecting probe comprises at least two recessed portions having different depths.

Further preferably, the biological information detecting probe is formed from Si, Ge, SIC, or diamond.

In one example, the biological information measuring apparatus of the present invention is characterized by comprising the above-described biological information detecting probe, a light source for detection light, and an analyzing means for analyzing the detection light passed through a living tissue and introduced into the biological information detecting probe, and in that the biological information measuring apparatus acquires biological information based on an analysis result obtained from the analyzing means.

Alternatively, the biological information measuring apparatus of the present invention may comprise the above-described biological information detecting probe, a light source for detection light, and an analyzing means for analyzing scattered light generated when the detection light is introduced into the living tissue, wherein the biological information measuring apparatus acquires biological information based on an analysis result obtained from the analyzing means.

In one example, the biological information measurement method of the present invention characterized by comprising a deforming step for deforming a portion of a living tissue by using the above-described biological information detecting probe, a detection light entering and exiting step for causing detection light to enter and exit the living tissue deformed in the deforming step, and a biological information analyzing step for acquiring biological information by analyzing the detection light passed through the deformed living tissue.

In an alternative example, the biological information measurement method of the present invention comprises a deforming step for deforming a portion of a living tissue by using the above-described biological information detecting probe, a detection light entering and exiting step for causing detection light to enter and exit the living tissue deformed in the deforming step, and a biological information analyzing step for acquiring biological information by analyzing scattered light generated when the detection light is introduced into the deformed living tissue.

The biological information detecting probe of the present invention may, as one example, comprise a recessed portion which is brought into intimate contact with a living tissue, wherein the recessed portion is formed so that light emitted from one side face of the recessed portion again enters the recessed portion from the other side face thereof after passing through the living tissue, and wherein the biological information detecting probe is formed from a material having a higher refractive index than the living tissue. With this configuration, since the depth at which the detection light passes through the living tissue can be controlled by adjusting the depth of the recessed portion, biological information concerning the target layer in the living tissue can be measured easily and with high sensitivity by using the above biological information detecting probe. Furthermore, since much of the detection light introduced into the living tissue can be fed back to the biological information detecting probe, damage to the living tissue can be reduced, and the problem of burning caused by the projection of the detection light can be eliminated.

It is preferable that there are a plurality of such recessed portions. In this case, the living tissue can be easily raised when the probe is placed in intimate contact with the living tissue.

It is also preferable that there are at least two recessed portions having different depths. Using this biological information detecting probe, biological information at various depths of the living tissue can be obtained simultaneously.

Any suitable material can be used for the biological information detecting probe as long as it has a higher refractive index than the living tissue to be measured; examples of such material include Si, Ge, SiC, diamond, $SiO_2$, ZnSe, ZnS, and KrS. Among them, Si, Ge, SiC, or diamond is preferred because of their high refractive index, high transmittance at the infrared wavelength band, and excellent mechanical strength.

It is also preferable to coat the biological information detecting probe with a thin film of amorphous diamond or the like by plasma CVD or other suitable method, because reflection loss at the interface of the biological information detecting probe can then be reduced.

The biological information measuring apparatus, as one example, is characterized by comprising the above-described biological information detecting probe, a light source for detection light, and an analyzing means for analyzing the detection light passed through a living tissue and introduced into the biological information detecting probe, and in that the biological information measuring apparatus acquires biological information based on an analysis result obtained from the analyzing means.

Here, any suitable light source that emits light at the absorption wavelength of the substance to be measured can be used for the light source; examples include a globar light source sintered of carbonized silicon SiC in stick shape, a $CO_2$ laser light source, a tungsten lamp, etc. For the measurement of glucose, the global light source is preferred because it can cover a relatively wide wavelength range and can produce excellent light even at longer wavelengths of about 10 microns.

For the analyzing means, any suitable method can be used as long as it can measure various state changes caused by molecular vibrations that occur when the substance to be measured absorbs light; for example, a Fourier transform infrared spectroscopic analysis method or an opto-acoustic measurement method can be used.

The biological information measuring apparatus of the present invention, as an alternative example, is characterized by comprising the above-described biological information detecting probe, a light source for detection light, and an analyzing means for analyzing scattered light generated when the detection light is introduced into the living tissue, and in that the biological information measuring apparatus acquires biological information based on an analysis result obtained from the analyzing means.

Here, for the light source, any suitable light source can be used as long as it can emit light that undergoes scattering when it is introduced into the living tissue; examples include an argon laser, a YAG laser, and a semiconductor laser.

For the analyzing means, any suitable method can be used as long as it can measure various state changes caused by molecular vibrations that occur when the substance to be measured absorbs light; for example, Fourier transform Raman spectroscopy may be used.

The biological information measurement method of the present invention, as one example, is characterized by comprising a deforming step for deforming a portion of a living tissue by using the above-described biological information detecting probe, a detection light entering and exiting step for causing detection light to enter and exit the living tissue deformed in the deforming step, and a biological information analyzing step for acquiring biological information by analyzing the detection light passed through the deformed living tissue.

The biological information measurement method of the present invention, as an alternative example, is characterized by comprising a deforming step for deforming a portion of a living tissue by using the above-described biological information detecting probe, a detection light entering and exiting step for causing detection light to enter and exit the living tissue deformed in the deforming step, and a biological information analyzing step for acquiring biological information by analyzing scattered light generated when the detection light is introduced into the deformed living tissue.

Potential for Exploitation in Industry

As is apparent from the above description, the present invention can provide a biological information detecting probe and a biological information measuring apparatus that can press a light sensor against a surface of a living body in extremely good contacting relationship and can easily measure information concerning deep portions of the living body, and a biological information measurement method for implementing the same.

The present invention can also provide a biological information detecting probe and a biological information measuring apparatus that are easy to handle and can easily carry out highly accurate measurements while minimizing damage to a living tissue, and a biological information measurement method for implementing the same.

What is claimed is:

1. A biological information detecting probe by comprising:
   pressing means which is pressed against a living tissue;
   detection light emitting means of emitting detection light through light emission surface of said pressing means; and
   a detection light entrance which said detection light is introduced through a light detection surface of said pressing means;
   wherein:
   said light emission surface is substantially parallel to a first plane;
   said light detection surface is substantially parallel to a second plane;
   the first plane and the second plane form an angle of less than 180°;
   at least one of said detection light emitting means or said detection light entrance is formed from a material that has a higher refractive index than said living tissue such that;
   said detection light is capable of being passed rectilinearly through said living tissue placed in contact with said pressing means and is capable of being introduced into said detection light entrance; and
   said detection light is refracted at least at one of said light emission surface or said light detection surface with said pressing means held pressed against said living tissue.

2. The biological information detecting probe as set forth in claim 1, further comprising:
   a living tissue pressing part which is pressed against said living tissue and thereby deforms a portion of said living tissue; and
   a base part which contacts a portion of said living tissue other than the portion thereof against which said living tissue pressing part is pressed;
   wherein said pressing means is formed extending over said living tissue pressing part and said base part.

3. The biological information detecting probe as set forth in claim 2, wherein said living tissue pressing part and/or said base part include secretion removing means of removing secretion released from said living tissue, said secretion removing means being located in a portion contacting said living tissue.

4. The biological information detecting probe as set forth in claim 3, wherein said secretion removing means is a hole or a groove.

5. The biological information detecting probe as set forth in claim 2, wherein:
   said detection light emitting means is provided in said living tissue pressing part, and
   said detection light entrance is provided in said base part.

6. The biological information detecting probe as set forth in claim in 5, wherein said detection light emitting means and/or said detection light entrance means include an optical waveguide.

7. The biological information detecting probe as set forth in claim 6, wherein said optical waveguide has a Y-branch shape or a plate-like shape.

8. The biological information detecting probe as set forth in claim 6, wherein:
   said optical waveguide in said detection light emitting means is for receiving external input light, and
   an end face of said optical waveguide, from which said detection light is not emitted, is formed so as to guide said input light to an end face from which said detection light is emitted.

9. The biological information detecting probe as set forth in claim 8, wherein said end face of said optical waveguide from which said detection light is not emitted totally reflects said input light for input into said optical waveguide.

10. The biological information detecting probe as set forth in claim 8, wherein:
    all or part of said end face of said optical waveguide from which said detection light is not emitted has a grating structure, and
    said grating structure diffracts said input light for input into said optical waveguide.

11. The biological information detecting probe as set forth in claim 6, wherein said optical waveguide is formed from a material selected from a group consisting germanium, silicon, and diamond.

12. The biological information detecting probe as set forth in claim 6, wherein said optical waveguide is surrounded with a cladding material.

13. The biological information detecting probe as set forth in claim 12, wherein the cladding material that has a lower refractive index than said optical waveguide.

14. The biological information detecting probe as set forth in claim 2, wherein:
    said detection light emitting means is provided in said base part, and
    said detection light entrance is provided in said living tissue pressing part.

15. The biological information detecting probe as set forth in claim 2, wherein said base part is formed from a silicon material.

16. The biological information detecting probe as set forth in claim 1, wherein said pressing means is formed from Si, Ge, SiC, or diamond.

17. A biological information measuring apparatus characterized by comprising:
    the biological information detecting probe as set forth in claim 1;
    a light source for said detection light; and
    analyzing means of analyzing said detection light passed through said living tissue and introduced into said biological information detecting probe;
    wherein said biological information measuring apparatus acquires biological information based on an analysis result obtained from said analyzing means.

18. The biological information measuring apparatus as set forth in claim 17, wherein said biological information detecting probe depresses said living tissue to a depth not greater than 5 mm.

19. The biological information measuring apparatus as set forth in claim 17, wherein:
said pressing means has a recessed portion;
said light emission surface is located on said recessed portion;
said light detection surface is located on said recessed portion;
said living tissue is fitted into said recessed portion with said pressing means held pressed against said living tissue;
said recessed portion is substantially in the shape of an inverted triangle in a cross section taken parallel to a light path of said detection light; and
said light source and the detection light emitting means are configured such that the light path of said detection light is one that is introduced into said living tissue from said detection light emitting means at an angle smaller than the angle formed by a straight line joining the bottom of said recessed portion to an edge of another recessed portion adjacent to said recessed portion, said edge being the part thereof nearest to said bottom, and a straight line passing through said edges of said plurality of recessed portions.

20. A biological information measuring apparatus comprising:
the biological information detecting probe as set forth in claim 1;
a light source for said detection light; and
analyzing means of analyzing scattered light generated when said detection light is introduced into said living tissue;
wherein said biological information measuring apparatus acquires biological information based on an analysis result obtained from said analyzing means.

21. The biological information detecting probe as set forth in claim 1, wherein said pressing means is formed from a material that has a higher refractive index than said living tissue.

22. The biological information detecting probe as set forth in claim 1, wherein said detection light emitting means and said detection light entrance are formed from a material that has a higher refractive index that said living tissue such that said detection light is capable of being passed rectilinearly through said living tissue placed in contact with said pressing means; and is capable of being introduced into said detection light entrance, wherein said detection light is refracted at said light emission surface and at said light detection surface with said pressing means held against said living tissue.

23. The biological information detecting probe as set forth in claim 1, wherein:
said pressing means having a recessed portion;
said light emission surface is located on said recessed portion;
said light detection surface is located on said recessed portion; and
said living tissue is fitted into said recessed portion with said pressing means held pressed against said living tissue.

24. The biological information detecting probe as set forth in claim 23, wherein said recessed portion is provided with a first light blocking film for blocking said detection light, said first light blocking film being formed on a part of said recessed portion other than the light emission surface and the light detection surface.

25. The biological information detecting probe as set forth in claim 23 or 24, wherein said recessed portion is substantially in the shape of an inverted triangle in a cross section taken parallel to a light path of said detection light.

26. The biological information measuring apparatus as set forth in claim 17, wherein said biological information detecting probe depresses said living tissue into a substantially curved shape.

27. The biological information detecting probe as set forth in claim 24, wherein:
the recessed portion is formed so as to have a face at its bottom; and
the first light blocking film is formed on the bottom of the recessed portion.

28. The biological information detecting probe as set forth in claim 24, wherein a plurality of the recessed portions are provided.

29. The biological information detecting probe as set forth in claim 28, further comprising a second light blocking film formed between the plurality of recessed portions.

30. The biological information detecting probe as set forth in claim 24 wherein said first light blocking film has a light absorbing or antireflection function.

31. The biological information detecting probe as set forth in claim 23, wherein a plurality of said recessed portions are provided.

32. The biological information detecting probe as set forth in claim 31, further comprising a light blocking film formed between said plurality of recessed portions.

33. The biological information detecting probe as set forth in claim 32, wherein said light blocking film has a light absorbing or antireflection function.

34. The biological information detecting probe as set forth in claim 31, wherein said plurality of recessed portions comprise at least two recessed portions having different depths.

35. The biological information detecting probe as set forth in claim 34, wherein said two recessed portions include:
a shallow recessed portion by which biological information concerning an epidermis of living tissue is capable of being detected; and
a deep recessed portion by which biological information concerning a dermis of the living tissue is capable of being detected.

36. The biological information detecting probe as set forth in claim 23, further comprising secretion removing means of removing secretion released from said living tissue;
wherein said secretion removing means is provided in the bottom of said recessed portion.

37. The biological information detecting probe as set forth in claim 36, wherein said secretion removing means is a hole or a groove.

38. A biological information detecting probe comprising:
pressing means having a recessed portion which is pressed against a living tissue;
detection light emitting means of emitting detection light through a light emission surface of said recessed portion; and
a detection light entrance into which said detection light is introduced through a light detection surface of said recessed portion;
wherein said recessed portion is provided with a light blocking film for blocking said detection light, said light blocking film being formed on a part of said recessed portion other than the light emission surface and the light detection surface.

39. The biological information detecting probe as set forth in claim 38, wherein said light blocking film has a light absorbing or antireflectlon function.

40. A biological information detecting probe comprising:

pressing means having a recessed portion which is pressed against a living tissue;

detection light emitting means of emitting detection light through a light emission surface of said recessed portion; and a detection light entrance into which said detection light is introduced through a light detection surface of said recessed portion;

wherein a plurality of said recessed portions are provided.

41. The biological information detecting probe as set forth in claim 40, further comprising a light blocking film formed between said plurality of recessed portions.

42. The biological information detecting probe as set forth in claim 41, wherein said light blocking film has a light absorbing or antireflection function.

43. The biological information detecting probe as set forth in claim 40, wherein said plurality of recessed portions comprise at least two recessed portions having different depths.

44. The biological information detecting probe as set forth in claim 40, wherein said two recessed portions include:

a shallow recessed portion by which biological information concerning an epidermis of living tissue is capable of being detected; and a deep recessed portion by which biological information concerning a dermis of the living tissue is capable of being detected.

45. A biological information detecting probe comprising:

pressing means having a recessed portion which is pressed against a living tissue;

detection light emitting means of emitting detection light through one part of said recessed portion;

a detection light entrance into which said detection light is introduced through a light detection surface of said recessed portion; and secretion removing means of removing secretion released from said living tissue;

wherein said secretion removing means is provided in the bottom of said recessed portion.

46. The biological information detecting probe as set forth in claim 45, wherein said secretion removing means is a hole or a groove.

* * * * *

UNITED STATES PATENT AND TRADEMARK OFFICE
CERTIFICATE OF CORRECTION

PATENT NO. : 6,882,872 B2
DATED : April 19, 2005
INVENTOR(S) : Shinji Uchida et al.

It is certified that error appears in the above-identified patent and that said Letters Patent is hereby corrected as shown below:

Title page,
Item [75], Inventors, "Shinji Uchida" delete "Neyagawa" and insert -- Osaka --; and "Kiyoko Ooshima" delete "Shijonawate" and insert -- Osaka --.

Signed and Sealed this

Eleventh Day of October, 2005

JON W. DUDAS
*Director of the United States Patent and Trademark Office*